(12) United States Patent
Sato et al.

(10) Patent No.: US 11,492,722 B2
(45) Date of Patent: *Nov. 8, 2022

(54) SEMICONDUCTOR APPARATUS AND POTENTIAL MEASURING APPARATUS

(71) Applicant: SONY SEMICONDUCTOR SOLUTIONS CORPORATION, Kanagawa (JP)

(72) Inventors: Masahiro Sato, Tokyo (JP); Machiko Kametani, Tokyo (JP); Jun Ogi, Kanagawa (JP); Yuri Kato, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 684 days.

This patent is subject to a terminal disclaimer.

(21) Appl. No.: 16/343,611

(22) PCT Filed: Nov. 17, 2017

(86) PCT No.: PCT/JP2017/041417
§ 371 (c)(1),
(2) Date: Apr. 19, 2019

(87) PCT Pub. No.: WO2018/101076
PCT Pub. Date: Jun. 7, 2018

(65) Prior Publication Data
US 2020/0048787 A1    Feb. 13, 2020

(30) Foreign Application Priority Data

Dec. 2, 2016    (JP) .............................. JP2016-235131

(51) Int. Cl.
*C25D 21/12*        (2006.01)
*G01N 27/30*        (2006.01)
(Continued)

(52) U.S. Cl.
CPC ........... *C25D 21/12* (2013.01); *G01N 27/301* (2013.01); *G01N 27/416* (2013.01);
(Continued)

(58) Field of Classification Search
CPC ........ C25D 7/12; C25D 21/12; G01N 27/301; G01N 27/416; G01N 33/48785; G01N 33/48735; G01R 29/12
See application file for complete search history.

(56) References Cited

U.S. PATENT DOCUMENTS 5,846,708 A    12/1998  Hollis et al.
6,476,751 B1 *  11/2002  Krymski ............. H03M 1/1014
                                                                341/120
(Continued)

FOREIGN PATENT DOCUMENTS

CA         2743258 A1    5/2010
CN       102272593 A    12/2011
(Continued)

OTHER PUBLICATIONS

Office Action for JP Patent Application No. 2018-553776, dated Apr. 13, 2021, 02 pages of English Translation and 02 pages of Office Action.

(Continued)

*Primary Examiner* — Brian W Cohen
(74) *Attorney, Agent, or Firm* — Chip Law Group

(57) ABSTRACT

The present disclosure relates to a semiconductor apparatus and a potential measuring apparatus capable of preventing deterioration in signal characteristics due to parasitic capacitance caused by providing a configuration for realizing an electrode plating process when an electrode and an amplifier are provided on the same substrate. When a power source supplies a potential necessary for plating processing and a breaker reads a signal from liquid, and an amplifier amplifies (Continued)

and outputs the signal, the power source required for the plating processing is blocked with respect to the electrode. This is applicable to the potential measuring apparatus.

13 Claims, 15 Drawing Sheets

(51) Int. Cl.
    *G01R 29/12*     (2006.01)
    *H03F 1/52*     (2006.01)
    *G01N 33/487*     (2006.01)
    *G01N 27/416*     (2006.01)

(52) U.S. Cl.
    CPC ....... *G01N 33/48785* (2013.01); *G01R 29/12* (2013.01); *H03F 1/523* (2013.01); *G01N 33/48735* (2013.01)

(56) References Cited

U.S. PATENT DOCUMENTS

| | | | |
|---|---|---|---|
| 7,030,801 B2 * | 4/2006 | Luo | H03M 1/682 341/172 |
| 7,786,908 B2 * | 8/2010 | Yoshinaga | H03M 1/1023 341/172 |
| 10,852,292 B2 * | 12/2020 | Sato | G01N 33/48728 |
| 2012/0091011 A1 | 4/2012 | Graham et al. | |
| 2013/0300435 A1 | 11/2013 | Chi et al. | |
| 2014/0142458 A1 | 5/2014 | Leyde et al. | |
| 2014/0375338 A2 | 12/2014 | Chi et al. | |

FOREIGN PATENT DOCUMENTS

| | | |
|---|---|---|
| DE | 39333687 T2 | 10/2005 |
| EP | 3638173 A1 | 2/1995 |
| EP | 2356448 A1 | 8/2011 |
| JP | 06-078889 A | 3/1994 |
| JP | 2002-031617 A | 1/2002 |
| JP | 2004-004064 A | 1/2004 |
| JP | 2004-064650 A | 2/2004 |
| JP | 2012-508051 A | 4/2012 |
| JP | 2013-011482 A | 1/2013 |
| JP | 2013-092437 A | 5/2013 |
| JP | 2013-108831 A | 6/2013 |
| JP | 5769020 B2 | 8/2015 |
| JP | 5796373 B2 | 10/2015 |
| WO | 93/22678 A2 | 11/1993 |
| WO | 2010/055287 A1 | 5/2010 |
| WO | 2011/153216 A2 | 12/2011 |

OTHER PUBLICATIONS

Office Action for CN Patent Application No. 201780068778.8, dated Jun. 21, 2021, 11 pages of English Translation and 09 pages of Office Action.

Mestais, et al., "WIMAGINE: Wireless 64-Channel ECoG Recording Implant for Long Term Clinical Applications", IEEE, Transactions on Neural Systems and Rehabilitation Engineering, vol. 23, No. 1, Jan. 2015, pp. 10-21.

International Search Report and Written Opinion of PCT Application No. PCT/JP2017/041417, issued on Jan. 30, 2018, 09 pages of ISRWO.

Mestais, et al., "WIMAGINE: Wireless 64-Channel ECOG Recording Implant for Long Term Clinical Applications", Transactions on Neural Systems and Rehabilitation Engineering, IEEE, vol. 23, No. 1, Jan. 2015, pp. 10-21.

Extended European Search Report of EP Application No. 17875259.8, dated Nov. 14, 2019, 12 pages.

* cited by examiner

SEMICONDUCTOR APPARATUS AND POTENTIAL MEASURING APPARATUS

CROSS REFERENCE TO RELATED APPLICATIONS

This application is a U.S. National Phase of International Patent Application No. PCT/JP2017/041417 filed on Nov. 17, 2017, which claims priority benefit of Japanese Patent Application No. JP 2016-235131 filed in the Japan Patent Office on Dec. 2, 2016. Each of the above-referenced applications is hereby incorporated herein by reference in its entirety.

TECHNICAL FIELD

The present disclosure relates to a semiconductor apparatus and a potential measuring apparatus, and more particularly, to a semiconductor apparatus and a potential measuring apparatus capable of preventing electrostatic breakdown during manufacturing.

BACKGROUND ART

In recent years, a technology for measuring an action potential of nerve cells and contributing medical research regarding the nerve action has been required. For example, an electrode apparatus for measuring and recording the action potential of the nerve cells has been proposed (refer to Patent Documents 1 and 2).

CITATION LIST

Patent Document

Patent Document 1: Japanese Patent Application Laid-Open No. 06-078889
Patent Document 2: Japanese Patent Application Laid-Open No. 2002-031617

SUMMARY OF THE INVENTION

Problems to be Solved by the Invention

In the technologies described in Patent Documents 1 and 2, in a case where a configuration which can perform electrode plating processing at the time of manufacturing is provided, there is a possibility that the configuration which can perform the plating processing increases a wiring capacity when a potential is measured and signal characteristics are deteriorated after completion of the apparatus.

The present disclosure has been made in configuration of such circumstances, and particularly prevents deterioration in signal characteristics in potential measurement while providing a configuration for realizing plating processing in a potential measuring apparatus.

Solutions to Problems

A semiconductor apparatus according to one aspect of the present disclosure includes a reference potential generating unit and a reference potential electrode that supply a reference potential to liquid filled into a container, a read electrode and an amplifier that read a signal from the liquid, a potential supply unit that fills plating solution instead of the liquid in the container and supplies a predetermined potential to the reference potential electrode and the read electrode when plating processing is performed on the reference potential electrode and the read electrode, and a breaker that blocks the supply of the predetermined potential from the potential supply unit at a position close to the amplifier at a time of potential measurement when the container is filled with the liquid, the reference potential generating unit supplies the reference potential to the liquid, the read electrode reads a signal from the liquid, and the signal read by the amplifier is amplified and output, and supplies the predetermined potential from the potential supply unit when the container is filled with the plating solution and the plating processing is performed, in which the reference potential generating unit, the reference potential electrode, the read electrode, the amplifier, the potential supply unit, and the breaker are installed on a same substrate.

The breaker is a Field Effect Transistor (FET) switch and is controlled to be turned off at the time of the potential measurement to block the supply of the potential from the potential supply unit at a position close to the amplifier and is controlled to be turned on when the plating processing is performed so as to supply the predetermined potential from the potential supply unit.

The breaker can be a diode of which a cathode is connected to the potential supply unit and an anode is connected to the amplifier, and at the time of the potential measurement, it is possible that the potential supply unit supplies a first predetermined potential and blocks the supply of the potential from the potential supply unit at a position close to the amplifier, and when the plating processing is performed, it is possible that the potential supply unit supplies a second predetermined potential.

At the time of the potential measurement, it is possible that the potential supply unit supplies a potential higher than the reference potential as a first predetermined potential and blocks the supply of the potential from the potential supply unit at a position close to the amplifier, and when the plating processing is performed, it is possible that the potential supply unit supplies a potential lower than a potential of the plating solution as a second predetermined potential.

The potential supply unit can supply the predetermined potential from a power source of the amplifier.

An additional diode can be further included that has the same characteristics as the diode and is formed by a same process as the diode, and of which a cathode is connected to the anode of the diode and an anode is connected to a ground potential.

Another breaker can be included that blocks the supply of the predetermined potential from the potential supply unit at a position close to the reference potential generating unit at the time of the potential measurement and supplies the predetermined potential from the potential supply unit when the plating processing is performed.

It is possible that the another breaker is a Field Effect Transistor (FET) switch and is controlled to be turned off at the time of the potential measurement to block the supply of the potential from the potential supply unit at a position close to the reference potential generating unit and is controlled to be turned on when the plating processing is performed so as to supply the predetermined potential from the potential supply unit.

The another breaker can be another diode of which a cathode is connected to the potential supply unit and an anode is connected to the amplifier, and at the time of the potential measurement, it is possible that the potential supply unit supplies a first predetermined potential and blocks the supply of the potential from the potential supply unit at a position close to the amplifier, and when the plating processing is performed, it is possible that the potential supply unit supplies a second predetermined potential.

At the time of the potential measurement, it is possible that the potential supply unit supplies a potential higher than the reference potential as a first predetermined potential and blocks the supply of the potential from the potential supply unit at a position close to the amplifier, and when the plating processing is performed, it is possible that the potential supply unit supplies a potential lower than a potential of the plating solution as a second predetermined potential.

The potential supply unit can supply the predetermined potential from a power source of the amplifier.

Another additional diode can be further included that has same characteristics as the another diode and is formed by a same process as the another diode, of which a cathode is connected to the anode of the another diode and an anode is connected to a ground potential.

A potential measuring apparatus according to one aspect of the present disclosure includes a reference potential generating unit and a reference potential electrode that supply a reference potential to liquid filled into a container, a read electrode and an amplifier that read a signal from the liquid, a potential supply unit that fills plating solution instead of the liquid in the container and supplies a predetermined potential to the reference potential electrode and the read electrode when plating processing is performed on the reference potential electrode and the read electrode, and a breaker that blocks the supply of the predetermined potential from the potential supply unit at a position close to the amplifier at a time of potential measurement when the container is filled with the liquid, the reference potential generating unit supplies the reference potential to the liquid, the read electrode reads a signal from the liquid, and the signal read by the amplifier is amplified and output, and supplies the predetermined potential from the potential supply unit when the container is filled with the plating solution and the plating processing is performed, in which the reference potential generating unit, the reference potential electrode, the read electrode, the amplifier, the potential supply unit, and the breaker are installed on a same substrate.

According to one aspect of the present disclosure, a reference potential generating unit and a reference potential electrode supply a reference potential to liquid filled in a container, a read electrode and an amplifier read a signal from the liquid, a potential supply unit fills plating solution instead of the liquid in the container, when plating processing is performed on the reference potential electrode and the read electrode, a predetermined potential is supplied to the reference potential electrode and the read electrode, the liquid is filled in the container, the reference potential generating unit supplies a reference potential to the liquid, at the time of potential measurement when the read electrode reads the signal from the liquid and the amplifier amplifies and outputs the read signal, a breaker blocks supply of the predetermined potential from the potential supply unit at a position close to the amplifier, and when the plating solution is filled in the container and the plating processing is performed, the predetermined potential from the potential supply unit is supplied, and the reference potential generating unit, the reference potential electrode, the read electrode, the amplifier, the potential supply unit, and the breaker are installed on a same substrate.

Effects of the Invention

According to one aspect of the present disclosure, it is possible to prevent deterioration in signal characteristics at the time of potential measurement while providing a configuration for realizing plating processing in a potential measuring apparatus.

MODE FOR CARRYING OUT THE INVENTION

Figure 1:
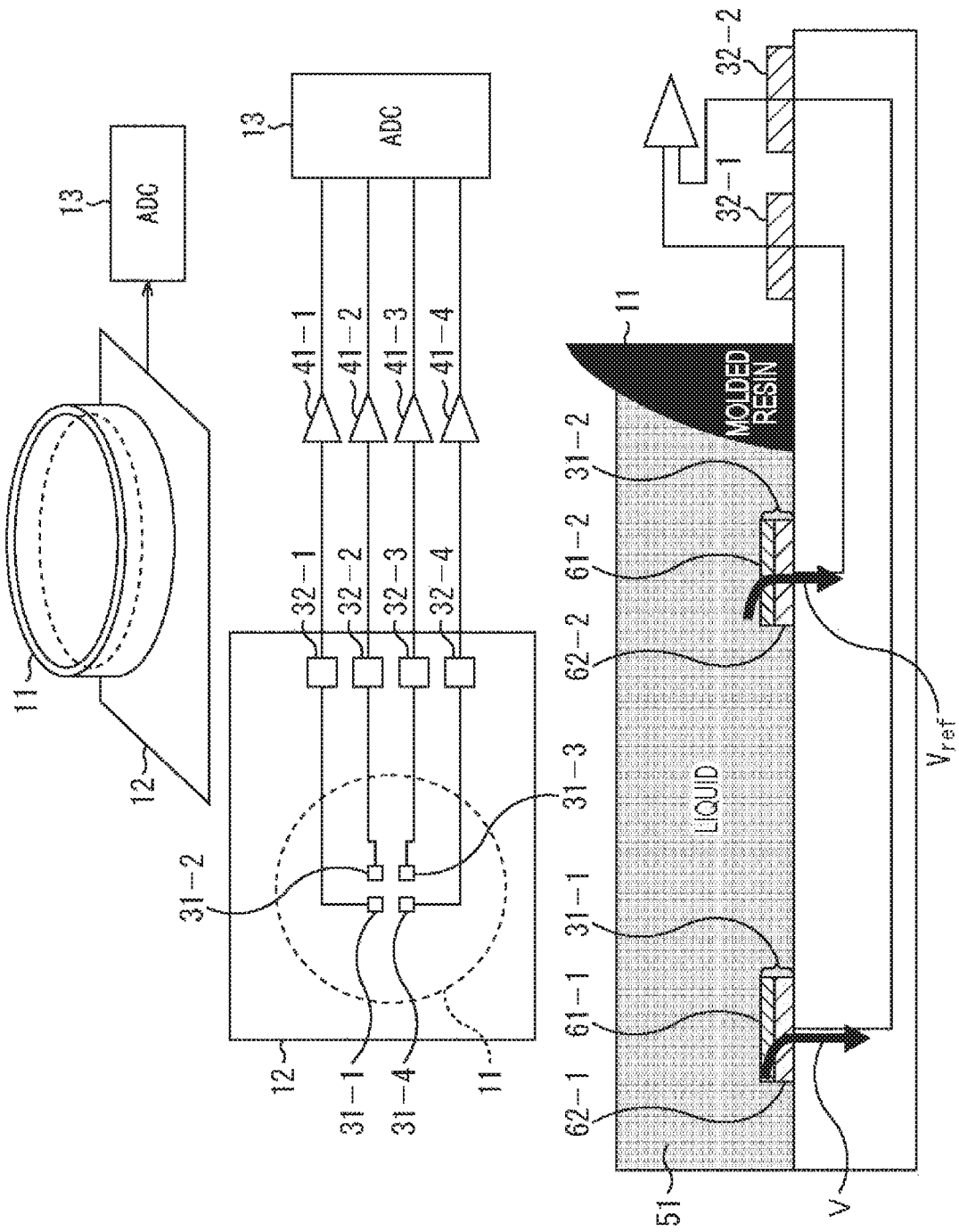
FIG. 1 is a diagram for explaining an exemplary configuration of a general potential measuring apparatus.

Hereinafter, preferred embodiments of the present disclosure will be described in detail with reference to the accompanying drawings. Note that, in the present specification and the drawings, components having substantially the same functional configuration are denoted with the same reference numeral so as to omit redundant description.

<Exemplary Configuration of General Potential Measuring Apparatus>

In description of a potential measuring apparatus according to the present disclosure, first, an exemplary configuration of a general potential measuring apparatus will be described with reference to FIG. 1. An upper part of FIG. 1 is a schematic perspective diagram of a potential measuring apparatus 1, a middle part of FIG. 1 is a wiring diagram corresponding to a top view of a petri dish 11 and an electrode substrate 12, and a lower part of FIG. 1 is a wiring diagram of a side cross section of the potential measuring unit 1.

As illustrated in the upper part of FIG. 1, the potential measuring apparatus 1 includes the petri dish 11, the electrode substrate 12, and an Analog Digital Converter (ADC) 13. The petri dish 11 includes molded resin and is filled with liquid 51 such as normal saline, and cells to be specimens are input to the petri dish 11. As illustrated in the middle part of FIG. 1, electrodes 31-1 to 31-4 are provided on a bottom surface of the petri dish 11 and respectively output measured potentials to amplifiers 41-1 to 41-4 via terminals 32-1 to 32-4. The amplifiers 42-1 to 42-4 amplify the measured potentials supplied from the electrodes 31-1 to 31-4 and output the measured potentials to the ADC 13. The ADC 13 converts the measured potentials which are amplified analog signals supplied from the amplifiers 42-1 to 42-4 into digital signals and output the digital signals to a subsequent apparatus.

In other words, a change in an action potential of a cell as a specimen in the liquid 51 is detected by the electrodes 31-1 to 31-4 and output to the ADC 13 via the terminals 32-1 to 32-4 and the amplifiers 41-1 to 41-4 as the digital signals.

Note that, in a case where it is not necessary for the electrodes 31-1 to 31-4, the terminals 32-1 to 32-4, and the amplifiers 41-1 to 41-4 to be particularly distinguished from each other, the electrodes 31-1 to 31-4, the terminals 32-1 to 32-4, and the amplifiers 41-1 to 41-4 are respectively and simply referred to as an electrode 31, a terminal 32, and an amplifier 41, and other components are similarly referred.

Furthermore, as illustrated in the lower part of FIG. 1, the electrodes 31-1 and 31-2 respectively include, for example, plating portions 61-1 and 61-2 and terminals 62-1 and 62-2, and plating processing is performed on the terminals 62-1 and 62-2 to add the plating portions 61-1 and 61-2, and the plating portions 61-1 and 61-2 have contact with the liquid 51. Note that, although not illustrated, the same applies to the electrodes 31-3 and 31-4.

That is, in a case where a local potential change around the electrode 31-1 is measured, the measured potential of the electrode 31-2 is read from the terminal 32-2, and an average potential is compared with the measured potential supplied from the electrode 32-1 via the terminal 32-1 as a reference potential Vref so as to measure a local potential change in the vicinity of the electrode 31-1.

However, in a case where a configuration which can perform electrode plating processing at the time of manufacturing is provided, there is a possibility that the configuration which can perform the plating processing increases a wiring capacity and that signal characteristics are deteriorated.

Therefore, the potential measuring apparatus according to the present disclosure prevents the deterioration in the signal characteristics in potential measurement while providing the configuration for realizing the plating processing.

<Exemplary Configuration of Top Surface of Potential Measuring Apparatus of Present Disclosure>

An exemplary configuration of the potential measuring apparatus which is a semiconductor apparatus according to the present disclosure will be described with reference to FIG. 2. Note that, in FIG. 2, a configuration of a substrate 110 of a potential measuring apparatus 101 is illustrated, and a configuration corresponding to the top view of the electrode substrate 12 in the middle part of FIG. 1 is illustrated.

Figure 2:
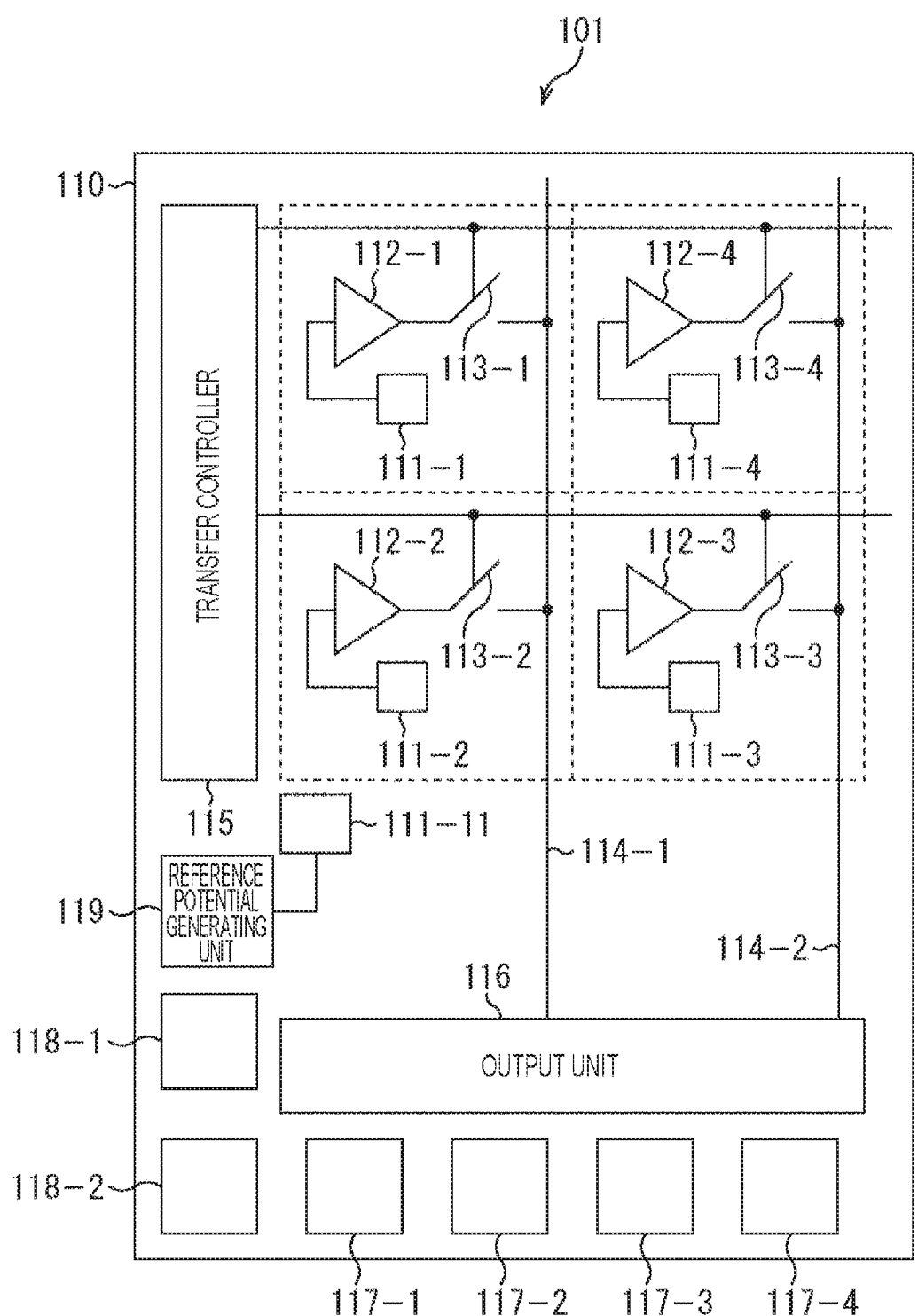
FIG. 2 is a diagram for explaining an exemplary configuration of a potential measuring apparatus according to the present disclosure.

The potential measuring apparatus 101 in FIG. 2 includes electrodes 111-1 to 111-4 and 111-11, amplifiers 112-1 to 112-4, switches 113-1 to 113-4, vertical transfer lines 114-1 and 114-2, a transfer controller 115, an output unit 116, terminals 117-1 to 117-4, terminals 118-1 and 118-2, and a reference potential generating unit 119.

The electrodes 111-1 to 111-4 and 111-11 are provided in the petri dish 11 including molded resin, and the electrodes 111-1 to 111-4 respectively correspond to the electrodes 31-1 to 31-4. The electrodes 111-1 to 111-4 have contact with liquid 131 (FIG. 3) in the petri dish 11 including molded resin, measure an action potential of a specimen in the liquid 131, and respectively transmit the action potentials to the amplifiers 112-1 to 112-4. Furthermore, the electrode 111-11 supplies a reference potential generated by the reference potential generating unit 119 to the liquid 131.

The amplifiers 112-1 to 112-4 are respectively provided directly below the electrodes 111-1 to 111-4 in the single substrate and respectively amplify voltages detected by the electrodes 111-1 to 111-4 and output the detected voltages to the switches 113-1 to 113-4.

The switches 113-1 and 113-2 are controlled to be turned on or off by the transfer controller 115. When being turned on, the switches 113-1 and 113-2 output outputs from the amplifiers 112-1 and 112-2 to the output unit 116 via the vertical transfer line 114-1. The switches 113-3 and 113-4 are controlled to be turned on or off by the transfer controller 115. When being turned on, the switches 113-3 and 113-4 output outputs from the amplifiers 112-3 and 112-4 to the output unit 116 via the vertical transfer line 114-2.

The output unit 116 converts amplified signals supplied from the amplifiers 112-1 to 112-4 via the vertical transfer lines 114-1 and 114-2 into digital signals and outputs the digital signals from the terminals 117-1 to 117-4.

The terminals 118-1 and 118-2 receive power and the like supplied from outside.

The reference potential generating unit 119 generates the reference potential and supplies the reference potential to the liquid 131 by the electrode 111-11. The electrode 111-11 has contact with the liquid 131 (FIG. 3) in the petri dish 11 including molded resin and supplies the reference potential to the liquid 131.

<Exemplary Configuration for Preventing Signal Deterioration Due to Wiring Capacity of Configuration for Performing Plating Processing>

Figure 3:
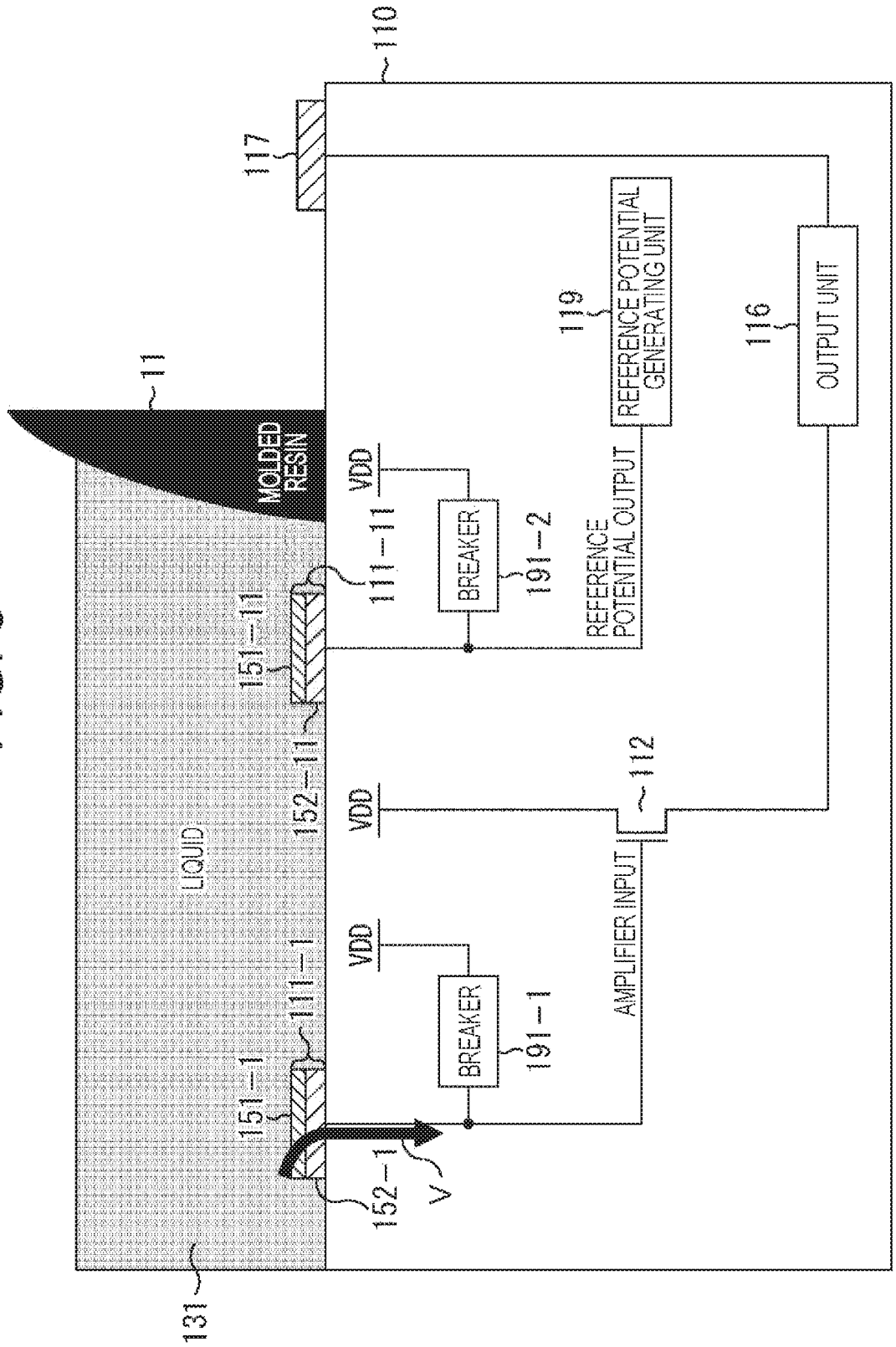
FIG. 3 is a diagram for explaining an exemplary configuration of the potential measuring apparatus in FIG. 2.

Next, an exemplary configuration for preventing signal deterioration due to a wiring capacity of the configuration for performing the plating processing will be described with reference to FIG. 3.

The electrodes 111-1 and 111-11 respectively include plating portions 151-1 and 151-11 including platinum and the like and metal portions 152-1 and 152-11. The electrode 111 includes only the metal portion 152 in general. However, since the metal portion 152 is a portion having contact with the liquid 131, the plating portion 151 is provided to prevent corrosion and the like.

The electrode 111-1 is an electrode which reads a signal, is connected to a gate of the amplifier 112 including an amplifying transistor, and transmits a potential of the liquid 131. The amplifier 112 includes an amplifying transistor, and a source and a drain of the amplifying transistor are connected to a power source VDD. The amplifier 112 outputs a voltage according to a potential V supplied from the electrode 111-1 to the gate to the output unit 116.

The output unit 116 analog-digital converts the output voltage which is the analog signal from the amplifier 112 and outputs the digital signal from the terminal 117.

Furthermore, the electrode 111-11 is an electrode which applies the reference potential output from the reference potential generating unit 119 to the liquid 131.

Breakers 191-1 and 191-2 are provided between the respective electrodes 111-1 and 111-11 and the power source VDD. The breakers 191-1 and 191-2 are connected to the power source VDD when the plating processing is performed on the electrodes 111-1 and 111-11 at the time of manufacturing and apply the voltage of the power source VDD to the electrodes 111-1 and 111-11 to form the plating portions 151-1 and 151-2.

Furthermore, after manufacturing, the breakers 191-1 and 191-2 measure potentials by the electrode 111-1, and when the reference potential is output by the electrode 111-11, the breakers 191-1 and 191-2 are in a high-impedance state and block conduction between the power source VDD and the electrodes 111-1 and 111-11.

In other words, the power source VDD which exists at the subsequent stage of the breakers 191-1 and 191-2 is a necessary component for an electrode plating process for forming the plating portions 151-1 and 151-2 at the time of manufacturing. However, after the manufacturing, signal transmission characteristics are deteriorated due to a capacitance caused by being parasitic in a circuit for applying voltages to the electrodes 111-1 and 111-11. Therefore, after the manufacturing, by blocking the conduction between the power source VDD and the electrodes 111-1 and 111-11, the breakers 191-1 and 191-2 prevent the deterioration in the signal transmission characteristics.

Note that, in the above description, an example has been described in which each of the breakers 191-1 and 191-2 is connected to the power source VDD. However, the electrodes 111-1 and 111-11 may be ground potentials in the electrode plating process. Therefore, in this case, the breakers 191-1 and 191-2 may be controlled to be turned on or off relative to the ground.

<First Specific Exemplary Configuration for Preventing Deterioration in Signal Transmission Characteristics Due to Wiring Capacity of Configuration for Performing Plating Processing>

Figure 4:
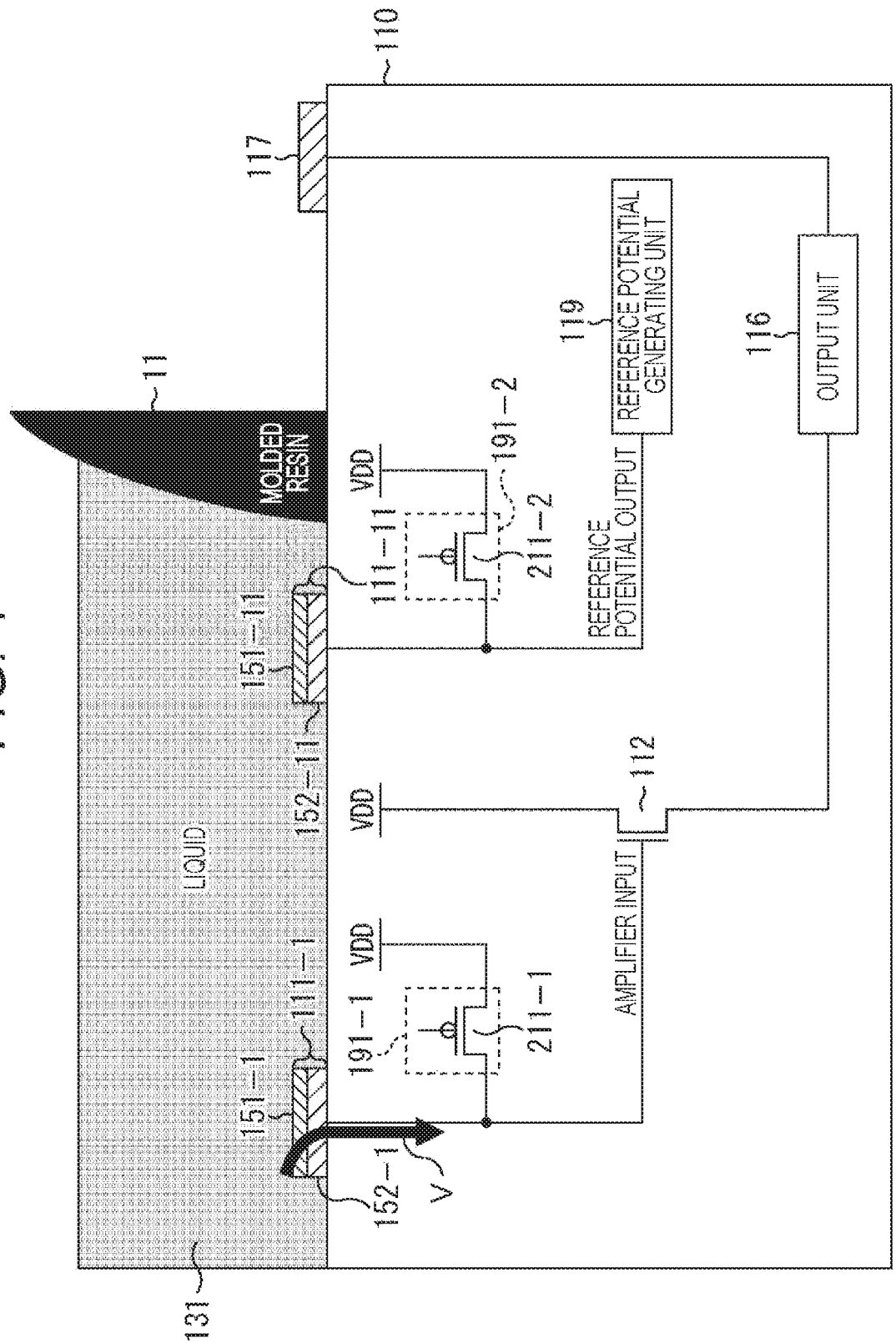
FIG. 4 is a diagram for explaining a first specific exemplary configuration of the potential measuring apparatus in FIG. 2.
Figure 5:
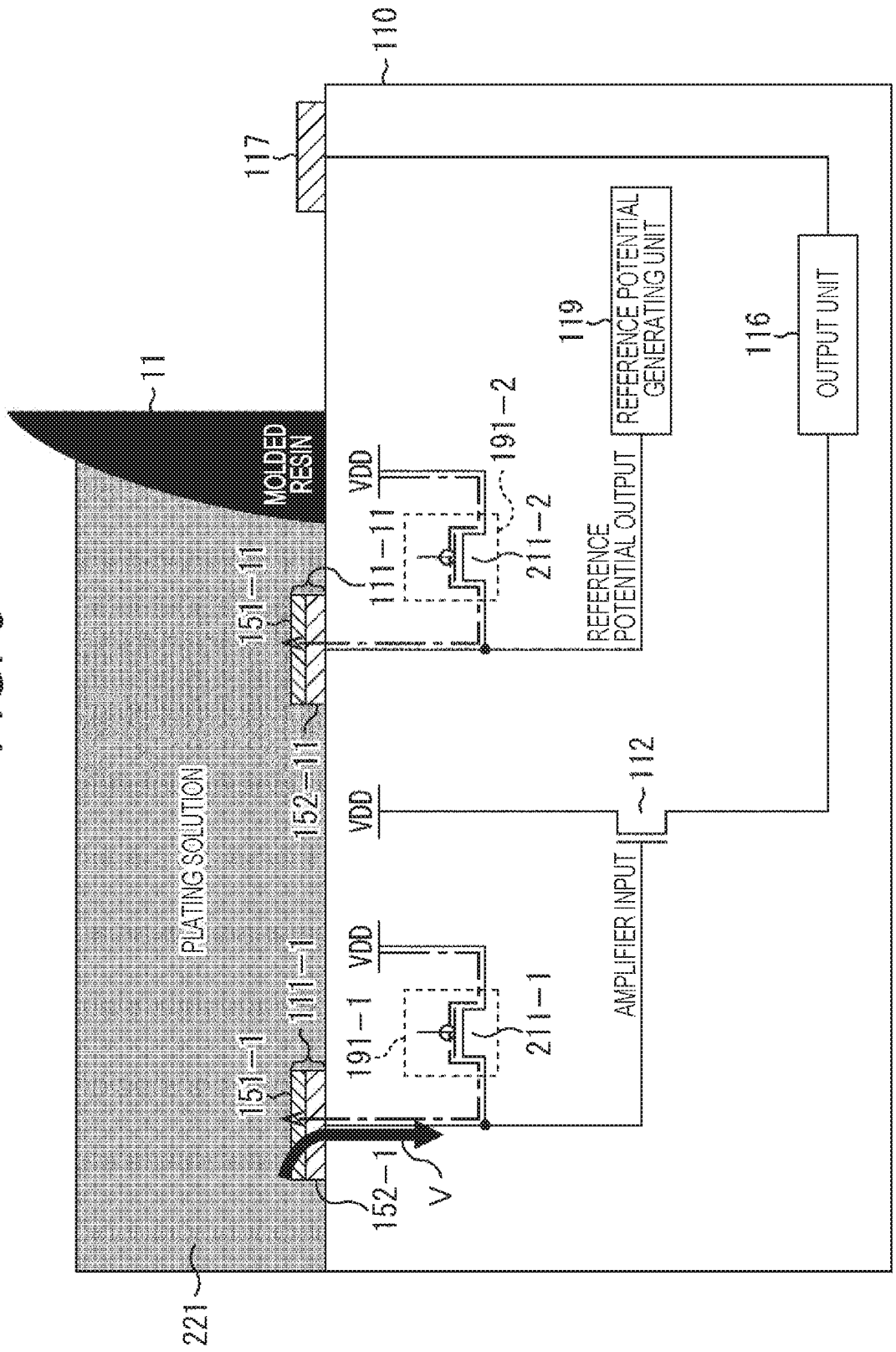
FIG. 5 is a diagram for explaining an operation of the potential measuring apparatus in FIG. 4.

Specifically, for example, as illustrated in FIG. 4, the breakers 191-1 and 191-2 respectively include Field Effect Transistor (FET) switches 2111-1 and 211-2.

In other words, in a case where the plating portions 151-1 and 151-11 are formed by the electrode plating process at the time of manufacturing, the petri dish 11 is filled with plating solution 221, and in addition, the FET switches 211-1 and 211-2 are controlled to be turned on. With this operation, as indicated by an alternate long and short dash line, the voltage of the power source VDD is applied to the electrodes 111-1 and 111-11. As a result, the plating processing is performed on the plating solution 221 on the metal portions 152-1 and 152-11 of the respective electrodes 111-1 and 111-11, and the plating portions 151-1 and 151-11 are formed.

Figure 6:
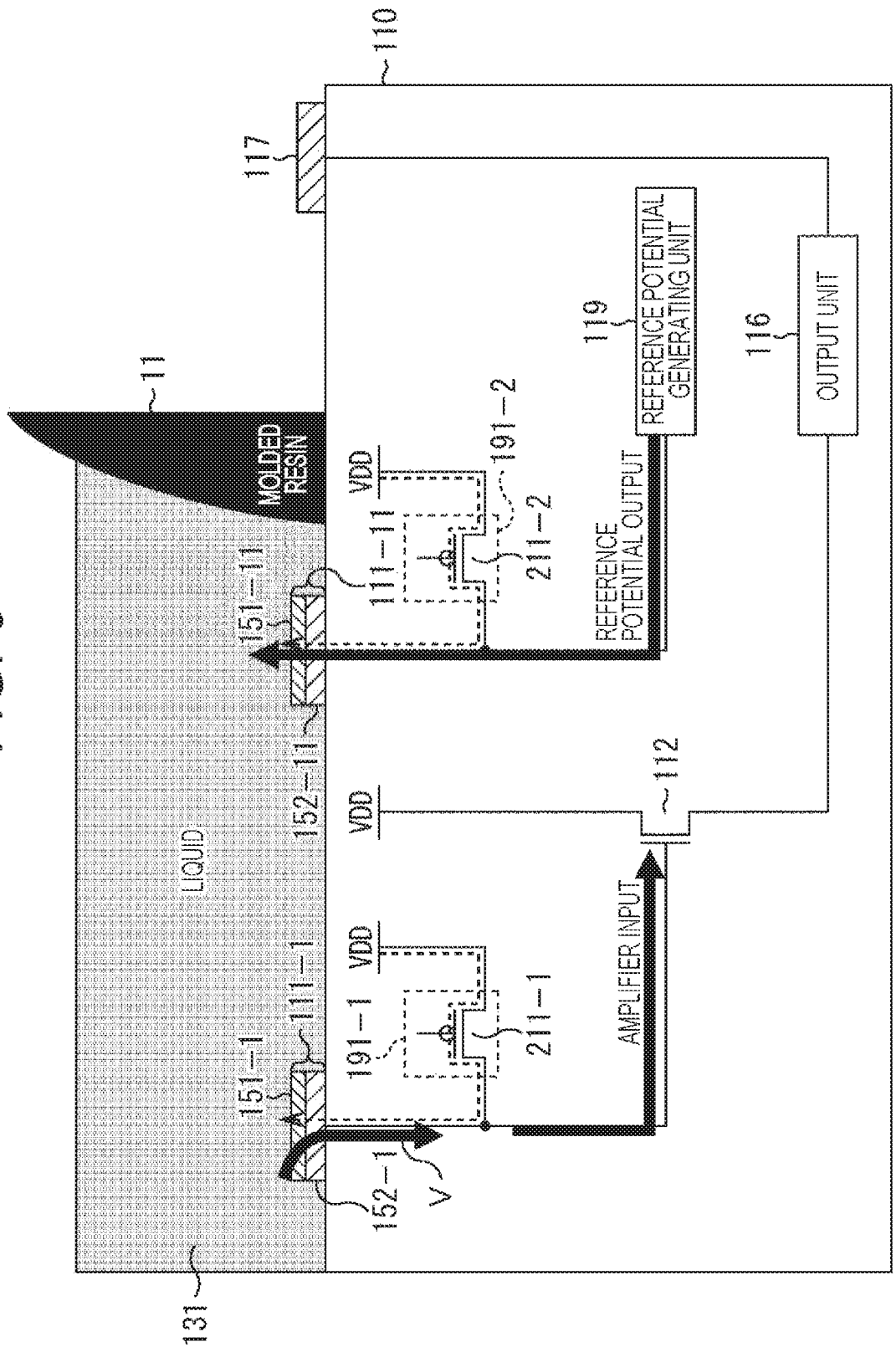
FIG. 6 is a diagram for explaining the operation of the potential measuring apparatus in FIG. 4.

Furthermore, in a case where the action potential of the specimen is measured after the manufacturing, as illustrated in FIG. 6, the petri dish 11 is filled with the liquid 131 in which the specimens are input, and the FET switches 211-1 and 211-2 are turned off. With this operation, as indicated by a dotted line, the potential of the power source VDD is blocked relative to the electrodes 111-1 and 111-11, and as indicated by a heavy line, the potential V is transmitted by the electrode 111-11, and the electrode 111-1 outputs the reference potential. As a result, the voltage from the power source VDD is not applied to the gate of the amplifier 112, and the signal from the electrode 111-1 is appropriately transmitted. Therefore, the deterioration in the signal transmission characteristics can be prevented.

<Second Specific Exemplary Configuration for Preventing Deterioration in Signal Transmission Characteristics due to Wiring Capacity of Configuration for Performing Plating Processing>

Figure 7:
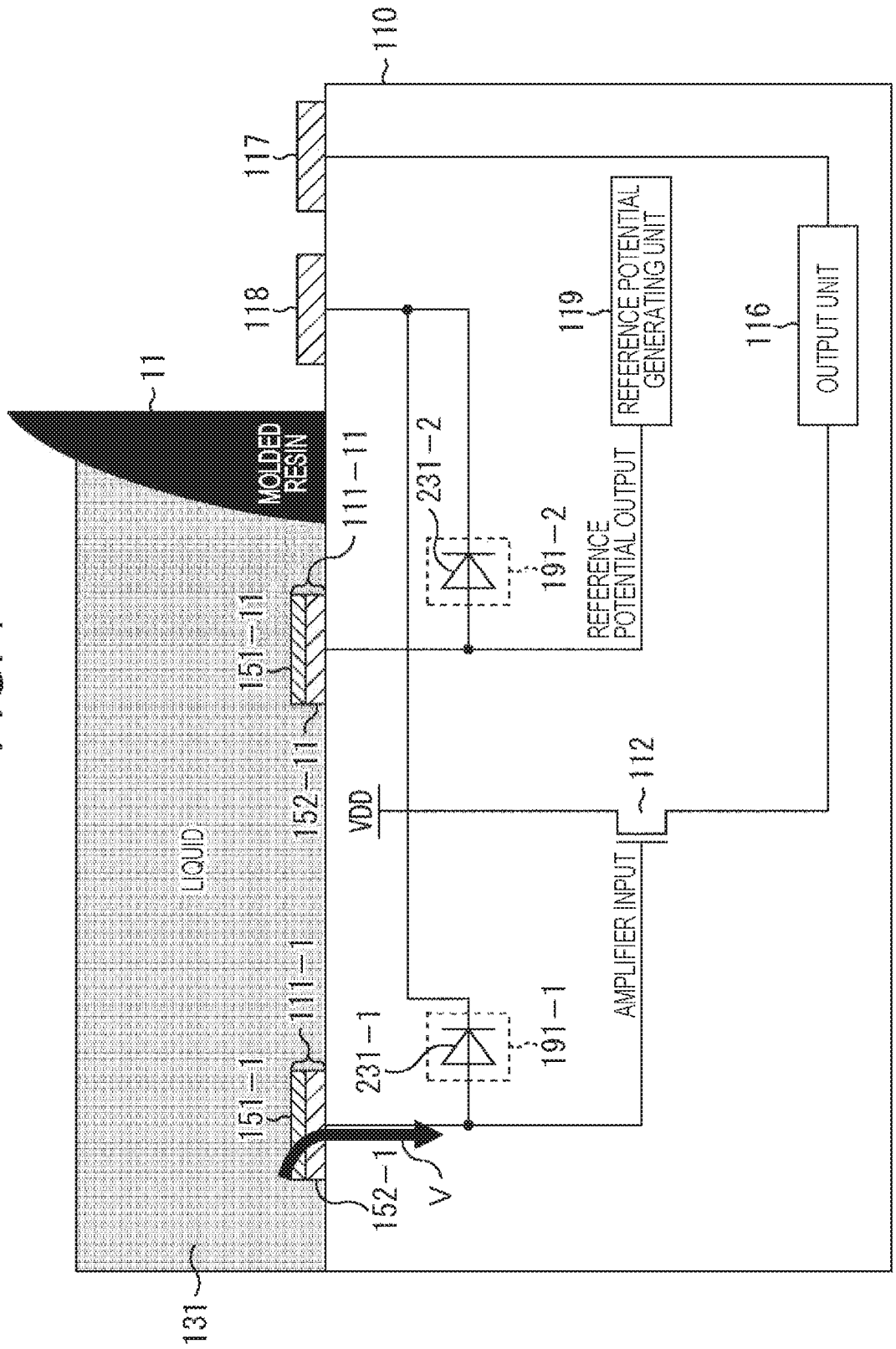
FIG. 7 is a diagram for explaining a second specific exemplary configuration of the potential measuring apparatus in FIG. 2.

In the above, an example has been described in which the FET switches 211-1 and 211-2 are provided as the specific configurations of the breakers 191-1 and 191-2. However, if other configuration can apply potentials necessary for the plating processing relative to the electrodes 111-1 and 111-11 in the electrode plating process and can block the potentials when the action potential is measured, the other configuration may be used. Therefore, as illustrated in FIG. 7, the specific configurations of the breakers 191-1 and 191-2 may be diodes 231-1 and 231-2. Here, anodes of the diodes 231-1 and 231-2 are respectively connected to the electrodes 111-1 and 111-11, and cathodes of the diodes 231-1 and 231-2 are connected to the terminal 118.

Figure 8:
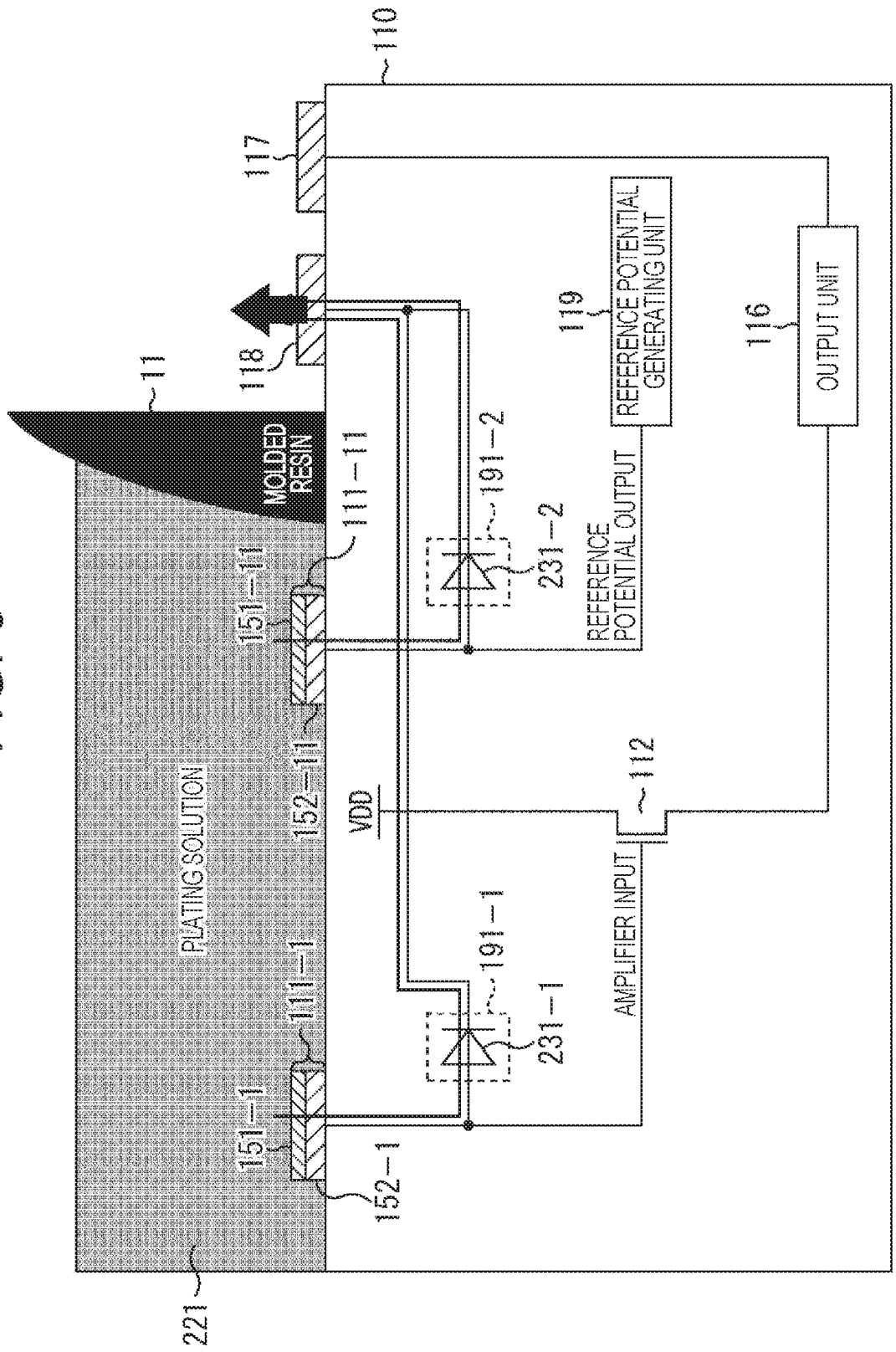
FIG. 8 is a diagram for explaining an operation of the potential measuring apparatus in FIG. 7.

With such a configuration, for example, in the electrode plating process, as illustrated in FIG. 8, in a state where the petri dish 11 is filled with the plating solution 221, a voltage with a potential lower than the potential of the plating solution 221 is applied to the terminal 118. According to such processing, as indicated by arrows in FIG. 8, current flows in a forward direction to the diodes 231-1 and 231-2, and the potentials of the electrodes 111-1 and 111-11 are lower than the potential of the plating solution 221, and accordingly, the plating portions 152-1 and 152-2 are formed.

Figure 9:
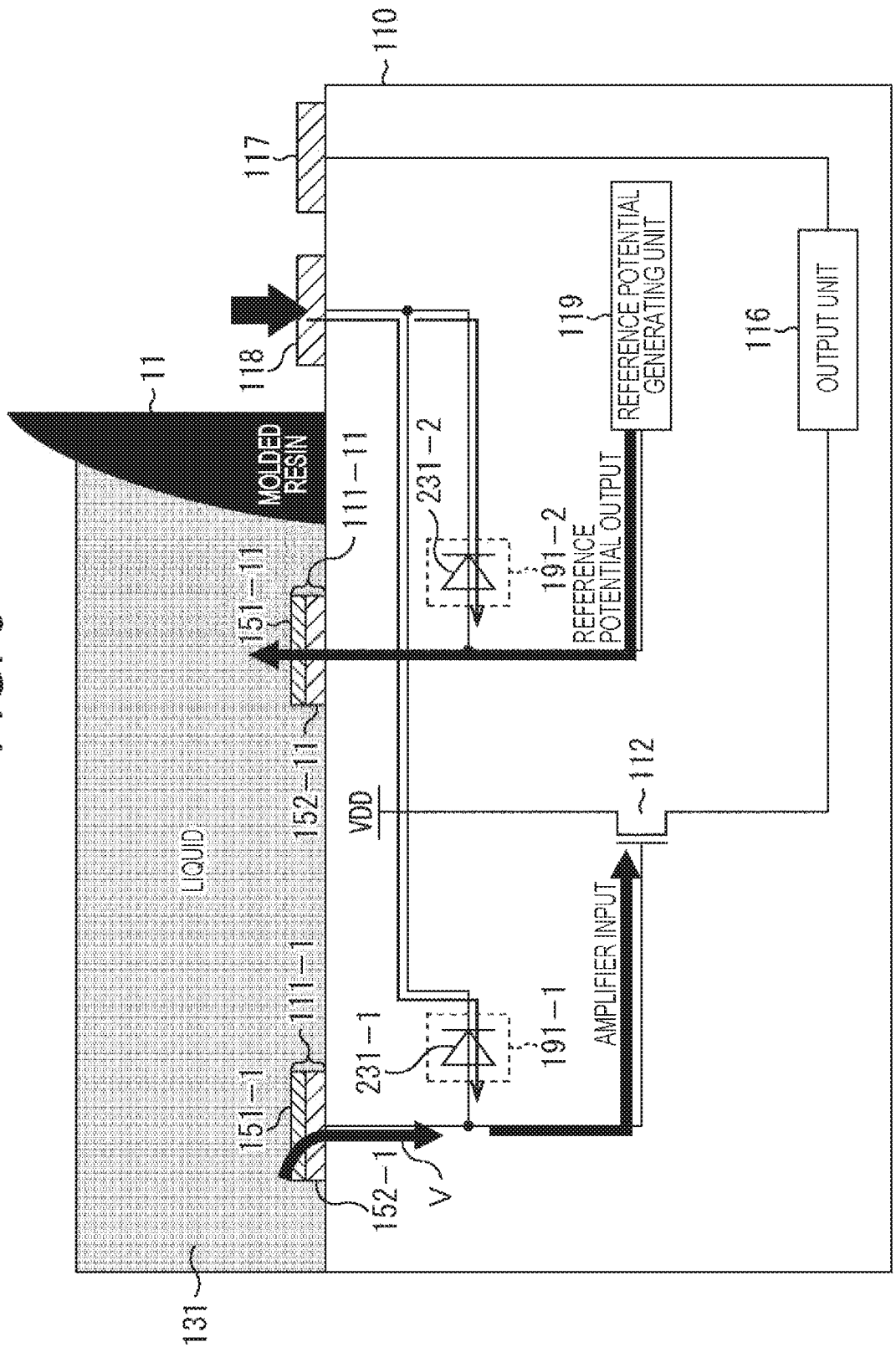
FIG. 9 is a diagram for explaining the operation of the potential measuring apparatus in FIG. 7.

On the other hand, when the action potential is measured, as illustrated in FIG. 9, a voltage having a potential higher than the reference potential is applied to the terminal 118. With this application, as indicated by solid arrows, a negative bias is applied to the diodes 231-1 and 231-2 so that the flow into the terminal 118 is blocked.

With this operation, as indicated by the solid arrows, the potential from the terminal 118 is blocked relative to the electrodes 111-1 and 111-11, and as indicated by a heavy line, the potential V is transmitted by the electrode 111-1, and the electrode 111-11 outputs the reference potential. As a result, since the signal from the electrode 111-1 is appropriately transmitted to the gate of the amplifier 112, the deterioration in the signal transmission characteristics can be prevented.

<Regarding Variation of Input Potentials to Amplifiers>

Figure 10:
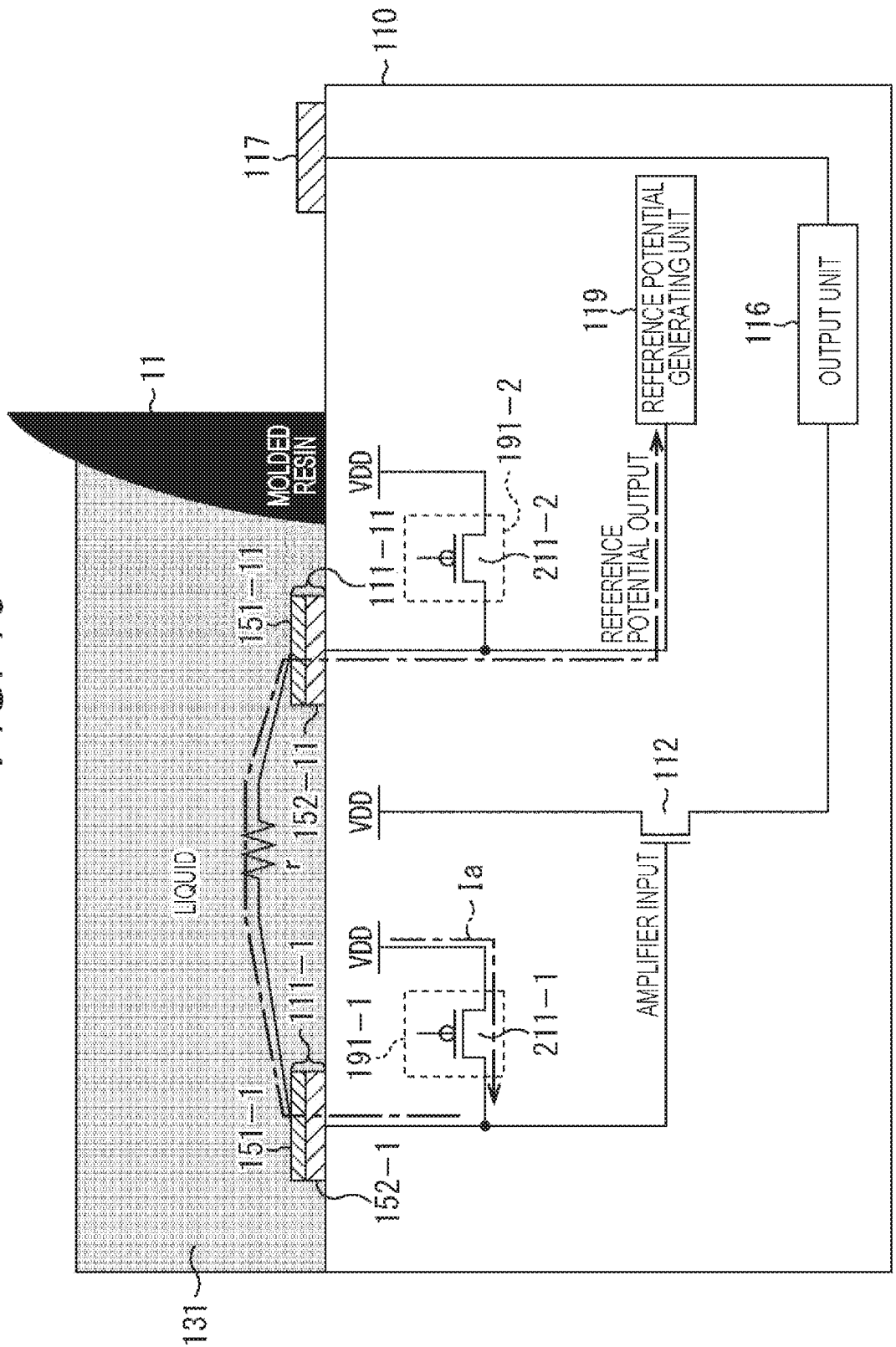
FIG. 10 is a diagram for explaining a leakage current in the potential measuring apparatus in FIG. 4.

When the action potential is measured by the potential measuring apparatus in FIG. 4, an impedance of the reference potential generating unit 119 is small. Therefore, as illustrated in FIG. 10, when a leakage current Ia is generated as indicated by an alternate long and short dash line, there is a possibility that a current to the reference potential generating unit 119 is generated, a potential difference from the reference voltage is generated by an external resistance r to a bias supply unit 171 by the liquid 131, and an input potential to the gate of the amplifying transistor configuring the amplifier 112 differs from the reference potential. Therefore, when the leakage current Ia and the external resistance r vary, the input potential to the gate of the amplifier 112 varies.

Figure 11:
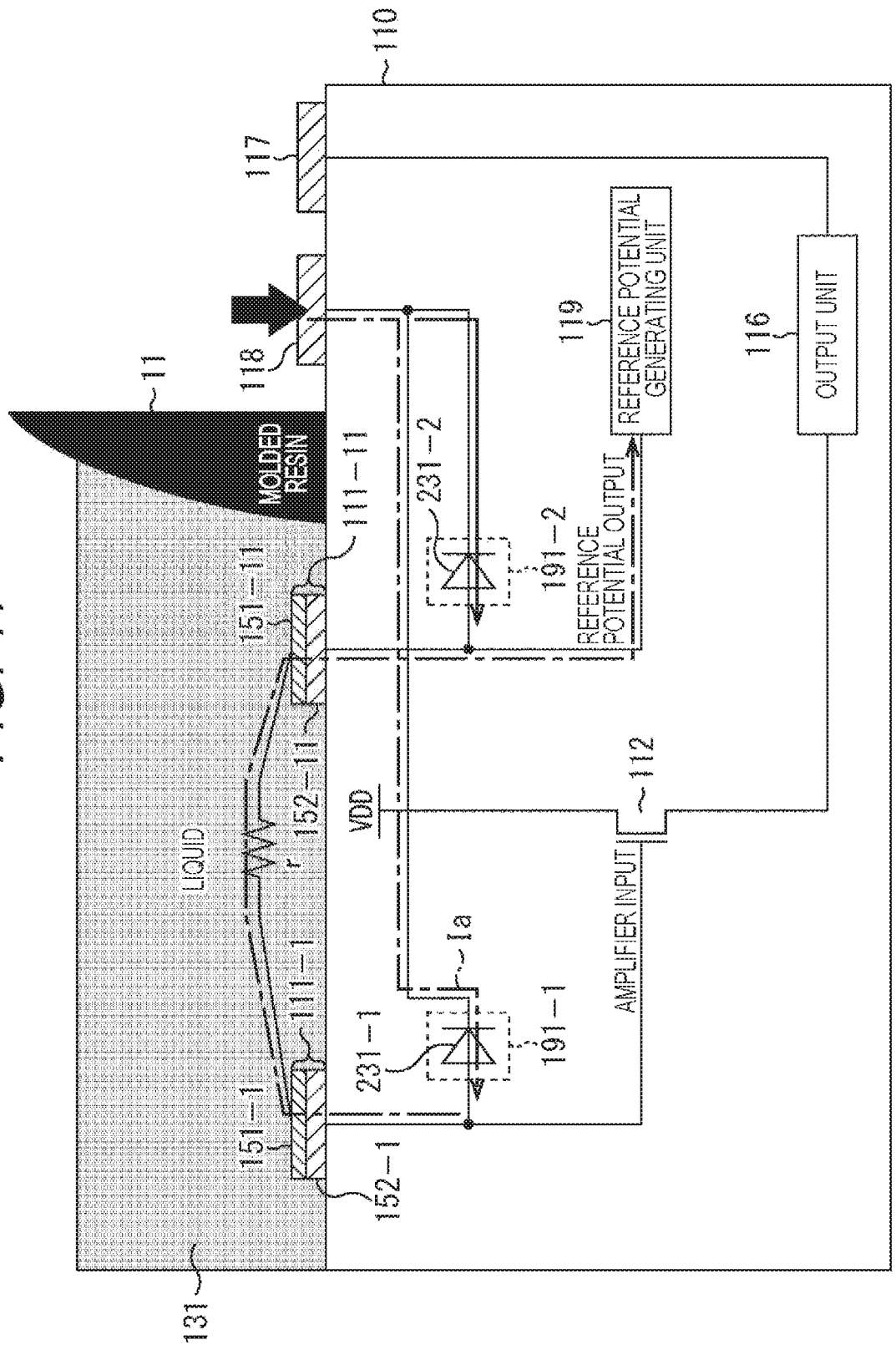
FIG. 11 is a diagram for explaining a leakage current in the potential measuring apparatus in FIG. 7.

Furthermore, similarly, when the action potential is measured by the potential measuring apparatus in FIG. 8, the impedance of the reference potential generating unit 119 is small. Therefore, as illustrated in FIG. 11, when the leakage current Ia is generated as indicated by an alternate long and short dash line, there is a possibility that the current to the reference potential generating unit 119 is generated, the potential difference from the reference voltage is generated by the external resistance r to the bias supply unit 171 by the liquid 131, and an input potential to the gate of the amplifying transistor configuring the amplifier 112 differs from the reference potential. Therefore, when the leakage current Ia and the external resistance r vary, the input potential to the gate of the amplifier 112 varies.

<Third Specific Exemplary Configuration for Preventing Deterioration in Signal Transmission Characteristics Due to Wiring Capacity of Configuration for Performing Plating Processing>

Figure 12:
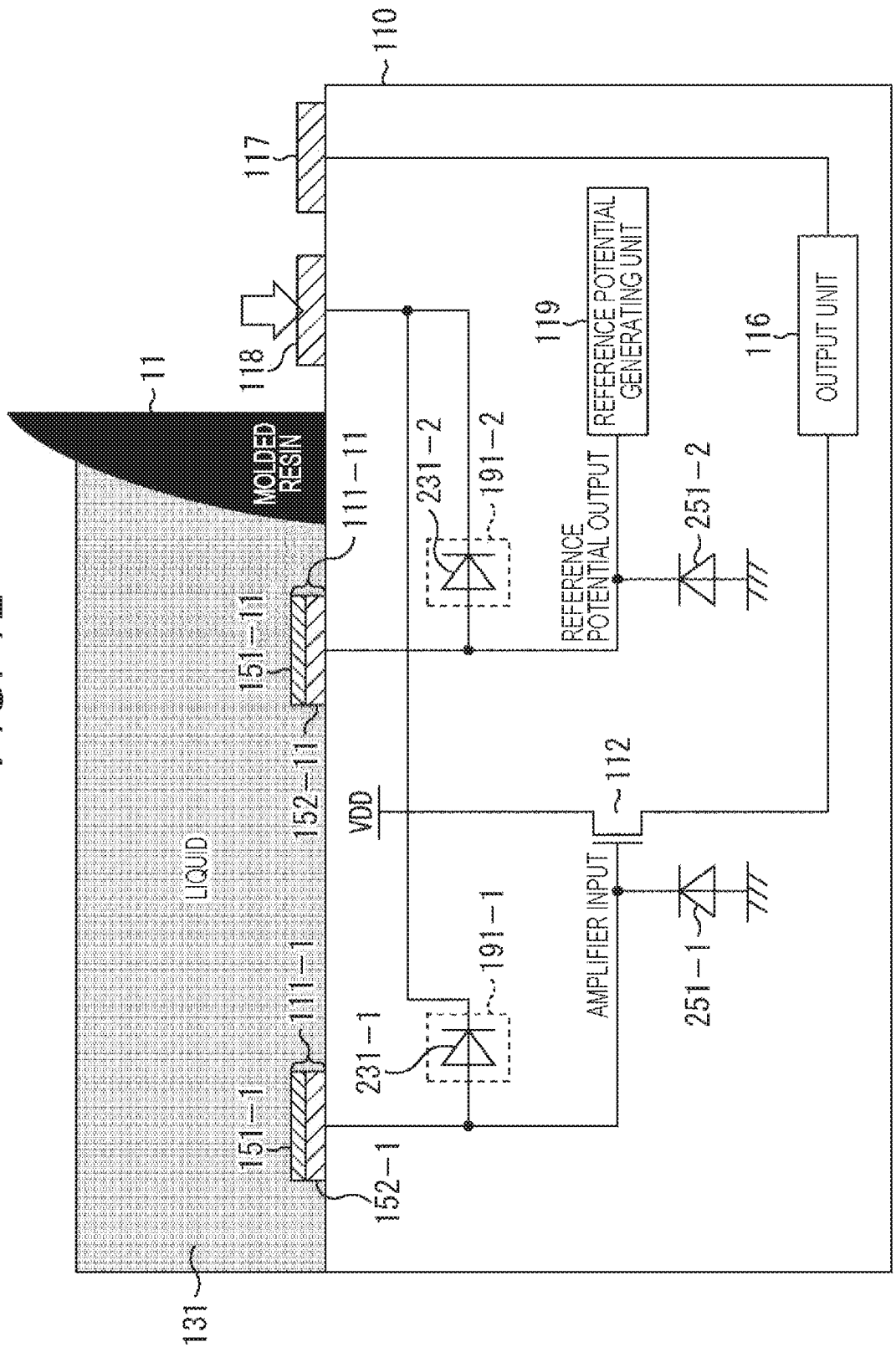
FIG. 12 is a diagram for explaining a third specific exemplary configuration of the potential measuring apparatus in FIG. 2.

Therefore, as illustrated in FIG. 12, in addition to the configuration in FIG. 8, a cathode of a diode 251-1 having the same IV conversion characteristics (current voltage conversion characteristics) as the diode 231-1 is connected to a previous stage of the gate of the amplifying transistor configuring the amplifier 112, and an anode is grounded. Furthermore, a cathode of a diode 251-2 having the same characteristics as the diode 231-2 is connected to a previous stage of the reference potential generating unit 119, and an anode is grounded.

Figure 13:
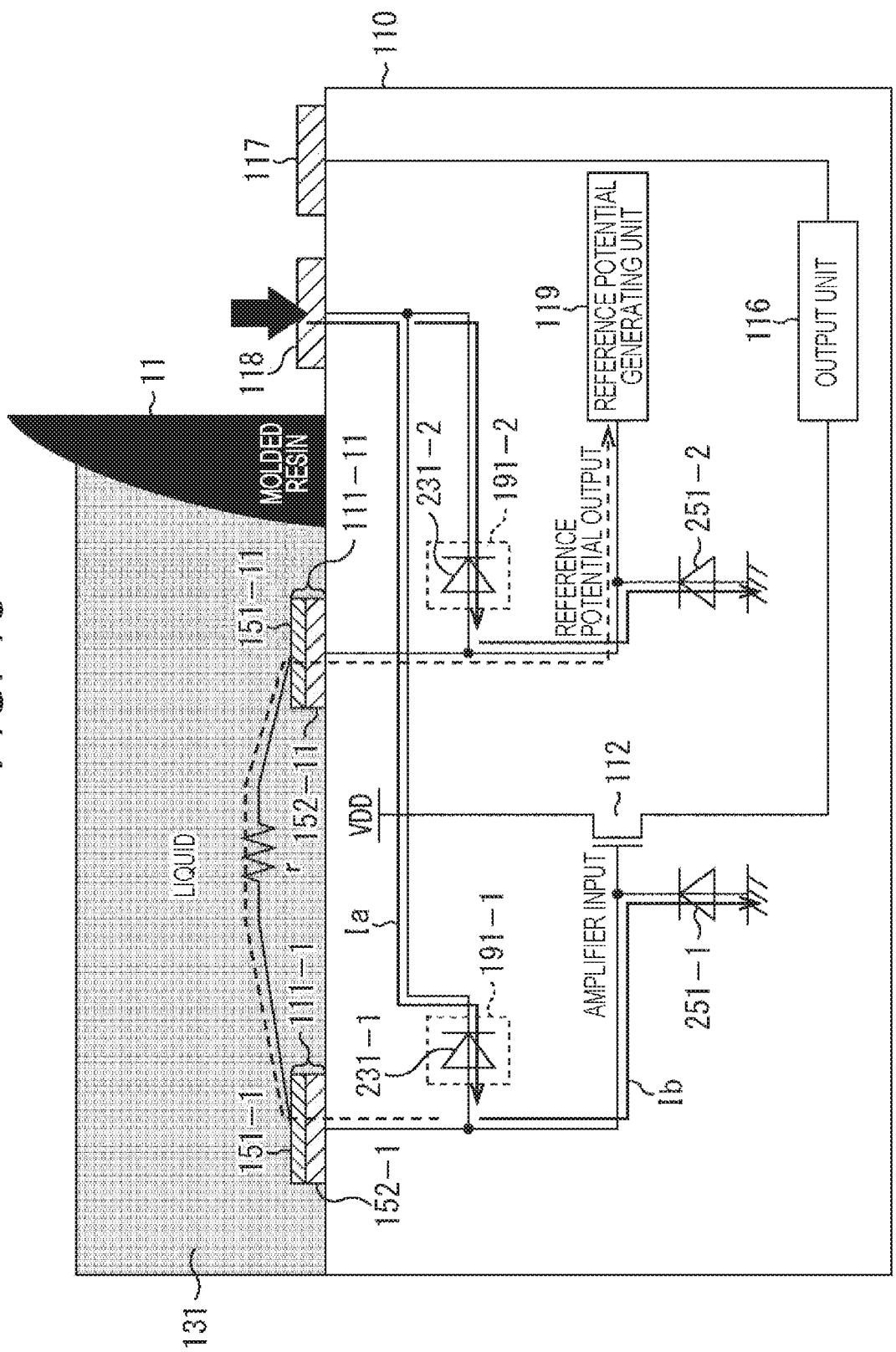
FIG. 13 is a diagram for explaining an operation of the potential measuring apparatus in FIG. 12.

With such a configuration, the diodes 231-1 and 251-1 having the equal characteristics are connected in series, and the diodes 231-2 and 251-2 having the equal characteristics are connected in series. As a result, as illustrated in FIG. 13, when the leakage currents Ia and Ib indicated by the solid lines are equal to each other, the potentials of the electrodes 111-1 and 111-11 are substantially the same, and the leakage current indicated by the dotted line is not flowed by an internal resistance r. Therefore, the input voltage to the gate of the amplifying transistor configuring the amplifier 112 can be stabilized.

Note that, by generating the diodes 231-1 and 251-1 and the diodes 231-2 and 251-2 in the same semiconductor process, the input voltage to the gate of the amplifying transistor configuring the amplifier 112 can be stabilized without increasing the number of processes in the manufacturing.

<Fourth Specific Exemplary Configuration for Preventing Deterioration in Signal Transmission Characteristics Due to Wiring Capacity of Configuration for Performing Plating Processing>

In the above, an example has been described in which the power supplied to the breakers 191-1 and 191-2 is external power supplied from the terminal 118 or the power source VDD which has been individually provided. However, the power may be supplied by the power source VDD of the amplifier 112.

Figure 14:
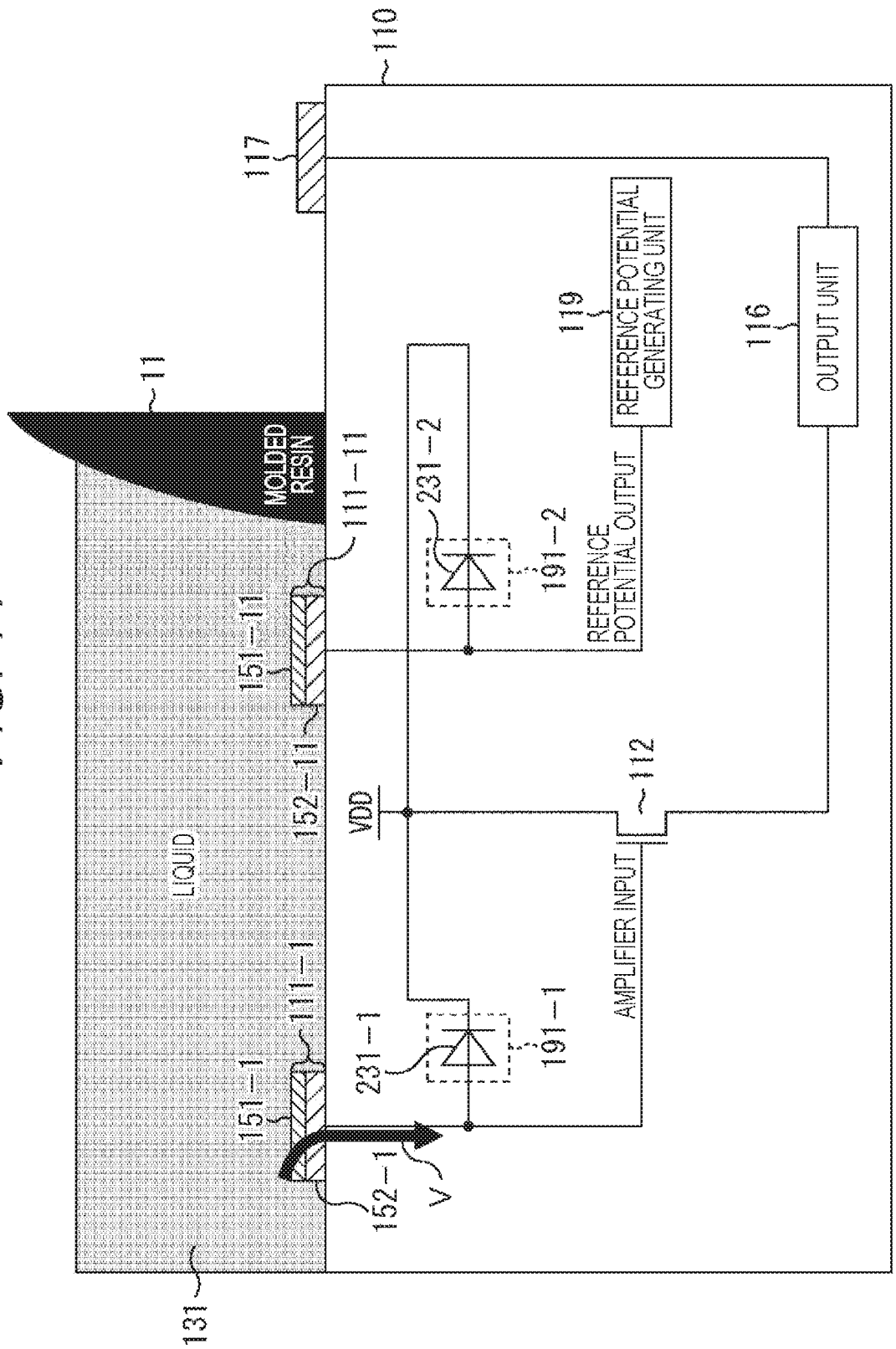
FIG. 14 is a diagram for explaining a fourth specific exemplary configuration of the potential measuring apparatus in FIG. 2.

In other words, as illustrated in FIG. 14, the cathodes of the diodes 231-1 and 231-2 are connected to the power source VDD of the amplifier 112. With this configuration, since it is not necessary to connect the external power and to increase wiring, the apparatus configuration can be further miniaturized.

Note that, since an operation of the potential measuring apparatus in FIG. 14 is similar to the operation of the potential measuring apparatus in FIG. 4, the description thereof will be omitted. Furthermore, the diodes 251-1 and 251-2 in FIG. 12 may be added to the configuration in FIG. 14.

<Modification>

In the above, as illustrated in FIG. 2, an example has been described in which the electrodes 111-1 to 111-4 and 111-11, the amplifiers 112-1 to 112-4, and the reference potential generating unit 119 are formed on the same substrate. However, if the electrode 111, the amplifier 112, and the reference potential 119 are formed on the same substrate, a configuration other than the configuration in which the electrodes 111-1 to 111-4 are arranged in two rows and two columns as illustrated in FIG. 2 may be used. For example, an electrode configuration in which electrodes are arranged in n rows and m columns may be used. Furthermore, the number of electrodes 111-11 used to supply the reference potential may be equal to or more than one.

Figure 15:
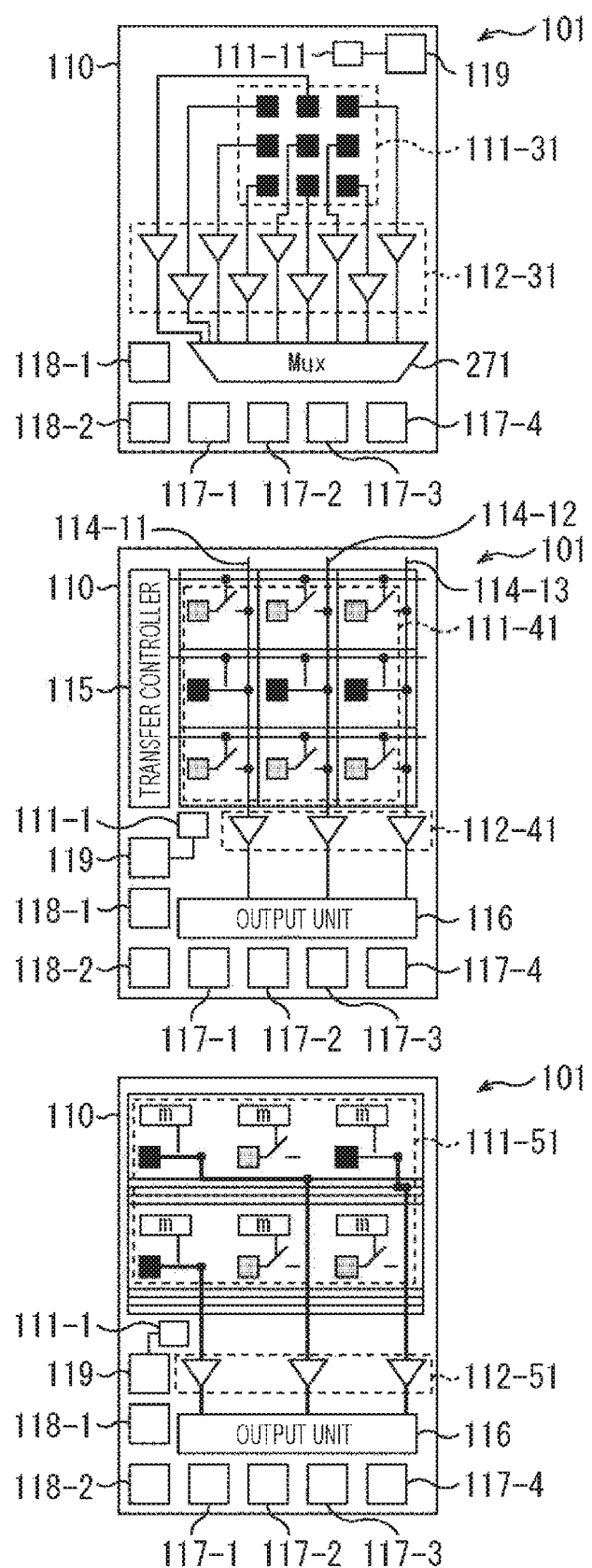
FIG. 15 is a diagram for explaining a modification of the potential measuring apparatus according to the present disclosure.

Furthermore, as illustrated in an upper part of FIG. 15, a configuration may be used in which an electrode group 111-31 including black electrodes arranged in an array of three rows and three columns and an amplifier group 112-31 of which amplifiers are respectively connected to the electrodes are included, the electrode group 111-31 and the amplifier group 112-31 are connected to a multiplexer (Mux) 271, and the multiplexer 271 time-divisionally outputs output signals.

Moreover, as illustrated in a middle part of FIG. 9, a configuration may be used in which an electrode group 111-41 including electrodes arranged in an array of three rows and three columns is controlled by the transfer controller 115 in unit of three rows, outputs are transferred to three vertical transfer lines 114-11 to 114-13, are amplified by an amplifier group 112-41 including amplifiers respectively provided on the vertical transfer lines 114-11 to 114-13, and are output to the output unit 116. However, in the middle part of FIG. 9, three gray electrodes arranged in the upper and the lower stages in FIG. 9 are controlled to be turned on or off by switches. However, three black electrodes in the middle stage do not have a switch and constantly perform output.

Furthermore, as illustrated in a lower part of FIG. 9, a configuration may be used in which a lower left black electrode, an upper left electrode, and an upper right electrode, that is, three electrodes in total of the electrode group 111-51 including electrodes arranged in an array of three rows and two columns are respectively connected to three amplifiers of an amplifier group 112-51. Note that, in the lower part of FIG. 9, each electrode included in the electrode group 111-51 includes a local memory denoted with "m" in FIG. 9.

Note that, the present disclosure may have the following configuration.

<1> A semiconductor apparatus including:

a reference potential generating unit and a reference potential electrode configured to supply a reference potential to liquid filled into a container;

a read electrode and an amplifier configured to read a signal from the liquid;

a potential supply unit configured to fill plating solution instead of the liquid in the container and supply a predetermined potential to the reference potential electrode and the read electrode when plating processing is performed on the reference potential electrode and the read electrode; and a breaker configured to block the supply of the predetermined potential from the potential supply unit at a position close to the amplifier at a time of potential measurement when the container is filled with the liquid, the reference potential generating unit supplies the reference potential to the liquid, the read electrode reads a signal from the liquid, and the amplifier amplifies and outputs the read signal, and to supply the predetermined potential from the potential supply unit when the container is filled with the plating solution and the plating processing is performed, in which the reference potential generating unit, the reference potential electrode, the read electrode, the amplifier, the potential supply unit, and the breaker are installed on a same substrate.

<2> The semiconductor apparatus according to <1>, in which the breaker is a Field Effect Transistor (FET) switch and is controlled to be turned off at the time of the potential measurement to block the supply of the potential from the potential supply unit at a position close to the amplifier and is controlled to be turned on when the plating processing is performed so as to supply the predetermined potential from the potential supply unit.

<3> The semiconductor apparatus according to <1> or <2>, in which
the breaker is a diode of which a cathode is connected to the potential supply unit and an anode is connected to the amplifier, and at the time of the potential measurement, the potential supply unit supplies a first predetermined potential and blocks the supply of the potential from the potential supply unit at a position close to the amplifier, and when the plating processing is performed, the potential supply unit supplies a second predetermined potential.

<4> The semiconductor apparatus according to <3>, in which
at the time of the potential measurement, the potential supply unit supplies a potential higher than the reference potential as a first predetermined potential and blocks the supply of the potential from the potential supply unit at a position close to the amplifier, and when the plating processing is performed, the potential supply unit supplies a potential lower than a potential of the plating solution as a second predetermined potential.

<5> The semiconductor apparatus according to <3>, in which
the potential supply unit supplies the predetermined potential from a power source of the amplifier.

<6> The semiconductor apparatus according to <3>, further including:
an additional diode having same characteristics as the diode and formed in a same process as the diode, of which a cathode is connected to the anode of the diode and an anode is connected to a ground potential.

<7> The semiconductor apparatus according to any one of <1> to <6>, further including:
another breaker configured to block the supply of the predetermined potential from the potential supply unit at a position close to the reference potential generating unit at the time of the potential measurement and supply the predetermined potential from the potential supply unit when the plating processing is performed.

<8> The semiconductor apparatus according to <7>, in which
the another breaker is a Field Effect Transistor (FET) switch and is controlled to be turned off at the time of the potential measurement to block the supply of the potential from the potential supply unit at a position close to the reference potential generating unit and is controlled to be turned on when the plating processing is performed so as to supply the predetermined potential from the potential supply unit.

<9> The semiconductor apparatus according to <7>, in which
the another breaker is another diode of which a cathode is connected to the potential supply unit and an anode is connected to the amplifier, and at the time of the potential measurement, the potential supply unit supplies a first predetermined potential and blocks the supply of the potential from the potential supply unit at a position close to the amplifier, and when the plating processing is performed, the potential supply unit supplies a second predetermined potential.

<10> The semiconductor apparatus according to <9>, in which
at the time of the potential measurement, the potential supply unit supplies a potential higher than the reference potential as a first predetermined potential and blocks the supply of the potential from the potential supply unit at a position close to the amplifier, and when the plating processing is performed, the potential supply unit supplies a potential lower than a potential of the plating solution as a second predetermined potential.

<11> The semiconductor apparatus according to <9>, in which
the potential supply unit supplies the predetermined potential from a power source of the amplifier.

<12> The semiconductor apparatus according to <9>, further including:
another additional diode having same characteristics as the another diode and formed in a same process as the another diode, of which a cathode is connected to the anode of the another diode and an anode is connected to a ground potential.

<13> A potential measuring apparatus including:
a reference potential generating unit and a reference potential electrode configured to supply a reference potential to liquid filled into a container;
a read electrode and an amplifier configured to read a signal from the liquid;
a potential supply unit configured to fill plating solution instead of the liquid in the container and supply a predetermined potential to the reference potential electrode and the read electrode when plating processing is performed on the reference potential electrode and the read electrode; and
a breaker configured to block the supply of the predetermined potential from the potential supply unit at a position close to the amplifier at a time of potential measurement when the container is filled with the liquid, the reference potential generating unit supplies the reference potential to the liquid, the read electrode reads a signal from the liquid, and the amplifier amplifies and outputs the read signal, and to supply the predetermined potential from the potential supply unit when the container is filled with the plating solution and the plating processing is performed, in which
the reference potential generating unit, the reference potential electrode, the read electrode, the amplifier, the potential supply unit, and the breaker are installed on a same substrate.

REFERENCE SIGNS LIST

101 Potential measuring apparatus
111, 111-1 to 111-5, 111-11 Electrode
112, 112-1 to 112-4 Amplifier
113-1 to 113-4 Switch
114, 114-1 to 114-3 Vertical transfer line
115 Transfer controller
116 Output unit
117, 117-1 to 117-4 Terminal
118 Terminal
119 Reference potential generating unit
131 Liquid
151, 151-1, 151-11 Plating portion
152, 152-1, 152-11 Metal portion
191, 191-1, 191-2 Breaker
211, 211-1, 211-2 FET switch
231, 231-1, 231-2 Diode
251, 251-1, 251-2 Diode

The invention claimed is:
1. A semiconductor apparatus, comprising:
a reference potential generating unit and a reference potential electrode configured to supply a reference potential to a liquid filled into a container;

a read electrode and an amplifier configured to read a signal from the liquid;

a potential supply unit configured to supply a specific potential to the reference potential electrode and the read electrode when a plating processing is performed on the reference potential electrode and the read electrode; and a first breaker configured to;

block the supply of the specific potential from the potential supply unit at a position close to the amplifier at a time of potential measurement when the container is filled with the liquid, the reference potential generating unit supplies the reference potential to the liquid, the read electrode reads a signal from the liquid, and the amplifier amplifies and outputs the read signal; and supply the specific potential from the potential supply unit when the container is filled with a plating solution and the plating processing is performed, wherein the reference potential generating unit, the reference potential electrode, the read electrode, the amplifier, the potential supply unit, and the first breaker are installed on a same substrate.

2. The semiconductor apparatus according to claim 1, wherein the first breaker is a Field Effect Transistor (FET) switch and is controlled to be turned off at the time of the potential measurement to block the supply of the potential from the potential supply unit at the position close to the amplifier and is controlled to be turned on when the plating processing is performed so as to supply the specific potential from the potential supply unit.

3. The semiconductor apparatus according to claim 1, wherein the first breaker is a first diode, a cathode of the first diode is connected to the potential supply unit and an anode of the first diode is connected to the amplifier, at the time of the potential measurement, the potential supply unit is configured to supply a first specific potential and block the supply of the potential from the potential supply unit at the position close to the amplifier, and when the plating processing is performed, the potential supply unit is configured to supply a second specific potential.

4. The semiconductor apparatus according to claim 3, wherein at the time of the potential measurement, the potential supply unit is further configured to supply a potential higher than the reference potential as the first specific potential and block the supply of the potential from the potential supply unit at the position close to the amplifier, and when the plating processing is performed, the potential supply unit is further configured to supply a potential lower than a potential of the plating solution as the second specific potential.

5. The semiconductor apparatus according to claim 3, wherein the potential supply unit is further configured to supply the specific potential from a power source of the amplifier.

6. The semiconductor apparatus according to claim 3, further comprising a second diode having same characteristics as the first diode, wherein a cathode of the second diode is connected to the anode of the first diode and an anode of the second diode is connected to a ground potential.

7. The semiconductor apparatus according to claim 1, further comprising:

a second breaker configured to block the supply of the specific potential from the potential supply unit at a position close to the reference potential generating unit at the time of the potential measurement and supply the specific potential from the potential supply unit when the plating processing is performed.

8. The semiconductor apparatus according to claim 7, wherein the second breaker is a Field Effect Transistor (FET) switch and is controlled to be turned off at the time of the potential measurement to block the supply of the potential from the potential supply unit at the position close to the reference potential generating unit and is controlled to be turned on when the plating processing is performed so as to supply the specific potential from the potential supply unit.

9. The semiconductor apparatus according to claim 7, wherein the second breaker is a third diode, a cathode of the third diode is connected to the potential supply unit and an anode of the third diode is connected to the amplifier, at the time of the potential measurement, the potential supply unit is further configured to supply a first specific potential and block the supply of the potential from the potential supply unit at the position close to the amplifier, and when the plating processing is performed, the potential supply unit is further configured to supply a second specific potential.

10. The semiconductor apparatus according to claim 9, wherein at the time of the potential measurement, the potential supply unit is further configured to supply a potential higher than the reference potential as the first specific potential and block the supply of the potential from the potential supply unit at the position close to the amplifier, and when the plating processing is performed, the potential supply unit is further configured to supply a potential lower than a potential of the plating solution as the second specific potential.

11. The semiconductor apparatus according to claim 9, wherein the potential supply unit is further configured to supply the specific potential from a power source of the amplifier.

12. The semiconductor apparatus according to claim 9, further comprising:

a fourth diode having same characteristics as the third diode, a cathode of the fourth diode is connected to the anode of the third diode and an anode of the fourth diode is connected to a ground potential.

13. A potential measuring apparatus, comprising:

a reference potential generating unit and a reference potential electrode configured to supply a reference potential to a liquid filled into a container;

a read electrode and an amplifier configured to read a signal from the liquid;

a potential supply unit configured to supply a specific potential to the reference potential electrode and the read electrode when a plating processing is performed on the reference potential electrode and the read electrode; and a breaker configured to;

block the supply of the specific potential from the potential supply unit at a position close to the amplifier at a time of potential measurement when the container is filled with the liquid, the reference potential generating unit supplies the reference potential to the liquid, the read electrode reads a signal from the liquid, and the amplifier amplifies and output the read signal; and supply the specific potential from the potential supply unit when the container is filled with a plating solution and the plating processing is performed, wherein the reference potential generating unit, the reference potential electrode, the read electrode, the amplifier, the potential supply unit, and the breaker are installed on a same substrate.

* * * * *